US006520952B1

(12) United States Patent
Jimenez

(10) Patent No.: US 6,520,952 B1
(45) Date of Patent: Feb. 18, 2003

(54) CERAMIC REINFORCED CATHETER

(75) Inventor: Oscar Jimenez, Coral Gables, FL (US)

(73) Assignee: Neich Medical Co., Ltd., Hong Kong (HK)

( * ) Notice: Subject to any disclaimer, the term of this patent is extended or adjusted under 35 U.S.C. 154(b) by 0 days.

(21) Appl. No.: 09/533,492

(22) Filed: Mar. 23, 2000

(51) Int. Cl.$^7$ .............................................. A61M 29/00
(52) U.S. Cl. ....................................... 604/524; 604/523
(58) Field of Search .................................. 604/523, 524

(56) References Cited

U.S. PATENT DOCUMENTS

| | | | |
|---|---|---|---|
| 4,636,346 A | * | 1/1987 | Gold et al. |
| 4,764,324 A | * | 8/1988 | Burnham .................... 264/103 |
| 4,898,591 A | * | 2/1990 | Jang et al. .................. 604/282 |
| 4,925,710 A | * | 5/1990 | Buck et al. ................. 428/34.5 |
| 5,100,379 A | * | 3/1992 | Wendell ....................... 604/51 |
| 5,380,298 A | | 1/1995 | Zabetakis et al. ........... 604/265 |
| 5,492,763 A | * | 2/1996 | Barry et al. ................. 428/457 |
| 5,647,858 A | | 7/1997 | Davidson |
| 5,782,910 A | | 7/1998 | Davidson ........................ 623/3 |
| 5,876,386 A | * | 3/1999 | Samson ....................... 604/524 |
| 5,908,413 A | * | 6/1999 | Lange et al. ................. 604/529 |
| 5,977,204 A | | 11/1999 | Boyan et al. ................ 523/113 |
| 6,217,566 B1 | * | 4/2001 | Ju et al. ...................... 604/526 |

FOREIGN PATENT DOCUMENTS

| | | |
|---|---|---|
| EP | 0894481 A2 | 2/1999 |
| EP | 0894481 A3 | 11/1999 |
| EP | 0982041 A1 | 3/2000 |

* cited by examiner

*Primary Examiner*—John Fox
(74) *Attorney, Agent, or Firm*—Thomas R. Vigil; Welsh & Katz, Ltd.

(57) ABSTRACT

The catheter includes a tubular body made from a composition including a ceramic, such as zirconium dioxide.

4 Claims, No Drawings

CERAMIC REINFORCED CATHETER

BACKGROUND OF THE INVENTION

1. Field of the Invention

The present invention relates to an improved material formulation for intravascular catheters, which may be used to extrude the body of a catheter or conduit to be introduced into a body, such as interventional guiding catheters, coronary catheters, drainage catheters, chemotherapy delivery catheters, radiology catheters or neuroradiology catheters, as well as the insulation or protective cover of electrical conduits, such as temporary leads for electrically stimulating the heart or other organs. The material formulation may also be used to provide conduits for surgical instruments used in keyhole operations such as cholisystectomy and laparoscopic tubal ligation, or for biopsy forceps.

2. Description of the Prior Art

Catheters are thin, flexible tubes, which are introduced into a vessel, such as a vein or artery, and guided to select sites, usually, but not exclusively, within the vascular system. In the case of an angiographic catheter, contrast media is injected into a vessel through the catheter's lumen to visualize the vessel's structure and anatomic changes within the vicinity of the distal opening of the catheter, for the purpose to diagnose disease and determine the direction, distribution and rate of flow.

Cardiac catheterization was first performed (and so named) by Claude Bernard in 1844. The subject was a horse, and both, the right and left heart ventricles were entered by a retrograde approach from the jugular vein and carotid artery. See Counard, Andre û Nobel Lecture, Dec. 11, 1956, Elsevier Pub. Co., 1964 p. 529.

In 1929, Werner Forssmann was credited with being the first person to a pass a catheter into the heart of a living person, himself. See Forssman W: Die Sondierung des rechten Herzens. Klin. Wochenschr. 8: 2085,1929.

Catheters are designed and manufactured using biocompatible polymer materials, which are compounded with certain radiopaque salts, known as radiopaque media, to visualize or register the catheter within the human body using fluoroscopy or conventional X-ray imaging recorded on film or magnetic media. The blending of the radiopaque medium demands that the polymer (typically a thermoplastic compound) be molten and the radiopaque medium be uniformly mixed with the viscous polymer. This compounding procedure subjects the commonly used radiopaque media, such as bismuth subcarbonate, to temperatures close to their thermal decomposition, which in turn may initiate the breakdown of the compound's physical properties. Bismuth subcarbonate is a white powdery salt that will thermally decompose into yellow bismuth trioxide during a typical compounding temperature excursion. This is further aggravated during the extrusion of the catheter body when additional heating is experienced by both, the bismuth subcarbonate and the polymeric compound. Further thermal exposure of the extruded catheter during the manufacturing process will continue to cause the bismuth subcarbonate and polymer compound to deteriorate.

Other commonly used radiopaque media, such as barium sulfate ($BaSO_4$), are also known to break down during high temperature compounding. Advances in both diagnostic and interventional catheterization procedures require a higher level of product performance than in the past. These improvements in catheter design include as wire braiding, high performance plastics, etc. Despite the problems caused by heat exposure, the use of thermally stable radiopaque media to reinforce the catheter appears desirable, as it does improve the polymer compound and the subsequently extruded catheter body with longer than earlier expected shelf life.

The ideal material for a catheter body, in addition to its excellent bio- or hemocompatibility, is expected to have high strength, high pressure rating, high flow rate due to low hydraulic resistance, chemical and thermal stability over its long shelf life, radiopacity when the application demands it, and excellent torque transmission characteristics along its length, especially for angiographic applications. In addition, it should be possible to extrude the material into various shapes, resulting in thin and uniform walls, smooth lumina, and the extruded surface should be suitable for bonding to the other components of the catheter product.

A catheter coated with zirconium oxide is disclosed in U.S. Pat. No. 5,647,858.

SUMMARY OF THE INVENTION

The use of ceramics to reinforce certain composite structures is known. Ceramics are used as insulators in spark plugs due to their thermal stability and high mechanical and dielectric strength. Ceramics are also known to be extremely inert and biocompatible, certain ceramics are used in implantable prosthetic devices such as the ball of an artificial femur in a hip joint. The present invention utilizes a fine ceramic powder known as monoclinic zirconia (zirconium dioxide, $ZrO2$) as an ambifunctional radiopaque medium that may provide the required radiopacity and reinforce the polymeric compound for intravascular catheters.

DESCRIPTION OF THE PREFERRED EMBODIMENT(S)

In accordance with the teachings of the present invention, zirconia powder is blended with selected biocompatible polymer resin(s) at a sufficiently high temperature to melt the polymer, but without a corresponding chemical degradation of the radiopaque medium. The inert zirconia powder may be blended with several polymers of various chemical compositions and hardness to optimize the catheter's physical properties. For example, nylon may be blended with polyurethane and PEBAX in specific proportions; zirconia is then added to the blend to reinforce the compounded material mechanically and render the blend radiopaque.

The formulation may include the addition of oxidized polyethylene as an internal lubricant, to improve the dispersion and lubricity of the molten blend of polymer(s) and zirconia during compounding. The final ceramic-loaded compound exhibits higher tensile strength, depending on the level of ceramic reinforcement (percent by weight) added to the selected biocompatible polymer(s). A range of 20–65 percent by weight produces a mechanically reinforced and radiopaque material.

Further enhancement of the ceramic reinforcement may be obtained by pretreating the zirconia ceramic powder with a hybrid coupling agent, such as certain types of organic silanes, titanates or zirconates, prior to compounding. The resulting ôhybridized compound provides additional reinforcement by creating a chemical bond between the zirconia ceramic powder and the polymer matrix. A simplified illustration, using silane pretreatment of the zirconia ceramic powder prior to compounding, is shown below:

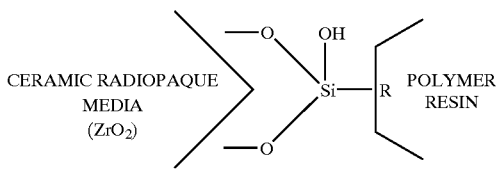

The chemical composition and concentration of the selected silane, titanate or zirconate may be adjusted depending on the resin(s). The objective is to select a coupling agent that is compatible with the selected resin(s) to optimize the physical performance of the final compound. Zirconium dioxide ($ZrO_2$) used as a ceramic reinforcement, with and without hybrid coupling agents, such as silanes, titanates or zirconates, does improve the physical properties of a single polymer or a polymer mixture (compound) as follows:

Zirconium dioxide eliminates polymer decomposition due to the thermal breakdown of the radiopaque medium during compounding.

Zirconium dioxide improves the tensile strength of the reinforced polymer compound.

Zirconium dioxide inhibits water absorption since ceramics, such as $ZrO_2$, are less hygroscopic than conventional radiopaque media.

Zirconium dioxide preserves radiopacity throughout the shelf life of the product since this radiopaque medium does not decompose with time and elevated temperature.

Zirconium dioxide enhances the torsional response of the catheter, as the inorganic ceramic powder is pre-treated with the organic resin to create a chemical bond between the components of the blend. (The desired torsional response is characterized by transmission of the torque applied at the proximal end of the catheter to its distal end.)

Zirconium dioxide reduces material shrinkage resulting from extrusion, as it is incompressible.

Zirconium dioxide allows the manufacturing of catheters with thinner walls without compromising high pressure rating and flow rates.

Zirconium dioxide improves bonding characteristics between the metal braiding and the catheterÆs polymer.

Zirconium dioxide enhances the catheter ability to be post-processed using adhesives and/or adding softer polymer segments to the catheter using thermal bonding techniques. Ceramics are excellent substrates for bonding, as their surface is oxygen rich as ceramics are oxides.

Zirconium dioxide promotes bonding of dissimilar materials with different hardnesses, as in bonding a soft distal portion to the catheter body.

Ceramic reinforcement provides a naturally inert and polished surface that is compatible with blood and other biological tissues; for example, to diminish hemolysis during vascular or heart catheterization.

Ceramic reinforcement stabilizes the addition of pigments as ceramics do not change color as they age or as a result of thermal exposure.

Ceramics provide a lubricious surface to reduce trauma between the catheter and the blood vessel or other tissues that it may contact.

According to the teachings of the present invention, a catheter material is created in the manner described above and then extruded into a catheter. The catheter so created then has the properties and advantages described above.

From the foregoing description, a catheter extruded from the ceramic loaded material described above has a number of advantages, some of which have been described above and others of which are inherent in the invention. Also, modifications can be made to the catheter composition of the present invention without departing from the teachings of the invention. Accordingly, the scope of the present invention is only to be limited as necessitated by the accompanying claims.

I claim:

1. A catheter including a tubular body made from a composition including a ceramic and nylon blended with polyurethane, a polyether block amide or other biocompatible polymer(s).

2. The catheter of claim 1 wherein said zirconium dioxide is first prepared as a ceramic powder and then pre-treated with a coupling agent selected from the group comprising silanes, titanates or zirconates prior to blending or compounding the polymer(s) in claim 4 with zirconium dioxide.

3. A method for making a tubular body for use as a catheter including the steps of:
    blending a ceramic with a plastic material including nylon blended with polyurethane, polyether block amide or other biocompatible polymer(s); and
    extruding the blended materials into a tubular body.

4. The method of claim 3 wherein said zirconium dioxide is first prepared as a ceramic powder and then pretreated with a coupling agent selected from one of: silanes, titantates or zirconates prior to blending the plastic material with the zirconium dioxide.

* * * * *